(12) United States Patent
Hobot et al.

(10) Patent No.: US 9,132,119 B2
(45) Date of Patent: Sep. 15, 2015

(54) CLONIDINE FORMULATION IN A POLYORTHOESTER CARRIER

(75) Inventors: Christopher M. Hobot, Tonka Bay, MN (US); Phillip E. McDonald, Plymouth, MN (US); Keith R. Hildebrand, Houlton, WI (US)

(73) Assignee: Medtronic, Inc., Minneapolis, MN (US)

( * ) Notice: Subject to any disclaimer, the term of this patent is extended or adjusted under 35 U.S.C. 154(b) by 1159 days.

(21) Appl. No.: 12/412,024

(22) Filed: Mar. 26, 2009

(65) Prior Publication Data

US 2009/0263448 A1    Oct. 22, 2009

Related U.S. Application Data

(60) Provisional application No. 61/046,201, filed on Apr. 18, 2008, provisional application No. 61/046,213, filed on Apr. 18, 2008.

(51) Int. Cl.
| | | |
|---|---|---|
| *A61F 2/00* | (2006.01) | |
| *A61K 31/415* | (2006.01) | |
| *A61K 9/00* | (2006.01) | |
| *A61K 9/16* | (2006.01) | |
| *A61K 9/06* | (2006.01) | |

(52) U.S. Cl.
CPC ............ *A61K 31/415* (2013.01); *A61K 9/0019* (2013.01); *A61K 9/0024* (2013.01); *A61K 9/0085* (2013.01); *A61K 9/1647* (2013.01); *A61K 9/06* (2013.01)

(58) Field of Classification Search
None
See application file for complete search history.

(56) References Cited

U.S. PATENT DOCUMENTS

| | | | |
|---|---|---|---|
| 3,190,802 A | 6/1965 | Zeile et al. | |
| 3,020,660 A | 8/1965 | Zeile et al. | |
| 4,765,974 A | 8/1988 | Tokuda et al. | |
| 5,175,052 A | 12/1992 | Tokuda et al. | |
| 5,447,947 A | 9/1995 | Campbell | |
| 5,484,607 A | 1/1996 | Horacek | |
| 5,635,204 A | 6/1997 | Gervirtz et al. | |
| 5,759,583 A | 6/1998 | Iwamoto | |
| 5,801,188 A | 9/1998 | Hassenbusch, III et al. | |
| 5,869,100 A | 2/1999 | Horacek | |
| 5,942,241 A | 8/1999 | Chasin | |
| 5,942,503 A | 8/1999 | Jung et al. | |
| 5,942,530 A | 8/1999 | Panetta et al. | |
| 5,945,416 A | 8/1999 | Shannon et al. | |
| 5,980,927 A * | 11/1999 | Nelson et al. | 424/425 |
| 6,030,642 A | 2/2000 | Horacek | |
| 6,069,129 A | 5/2000 | Sandberg | |
| 6,147,102 A | 11/2000 | Borgman | |
| 6,179,862 B1 | 1/2001 | Sawhney | |
| 6,248,345 B1 | 6/2001 | Goldenheim | |
| 6,287,588 B1 | 9/2001 | Shih | |
| 6,326,020 B1 | 12/2001 | Kohane | |
| 6,331,311 B1 | 12/2001 | Brodbeck | |
| 6,417,184 B1 | 7/2002 | Ockert | |
| 6,428,804 B1 | 8/2002 | Suzuki | |
| 6,451,335 B1 | 9/2002 | Goldenheim et al. | |
| 6,461,631 B1 | 10/2002 | Dunn | |
| 6,524,607 B1 | 2/2003 | Goldenheim | |
| 6,534,048 B1 | 3/2003 | Borgman | |
| 6,534,081 B2 | 3/2003 | Goldenheim | |
| 6,589,549 B2 | 7/2003 | Shih | |
| 6,630,155 B1 | 10/2003 | Chandrashekar | |
| 6,632,457 B1 | 10/2003 | Sawhney | |
| 6,773,714 B2 | 8/2004 | Dunn | |
| 6,921,541 B2 | 7/2005 | Chasin | |
| 6,992,110 B2 | 1/2006 | Kranzler et al. | |
| 7,287,983 B2 | 10/2007 | Han | |
| 7,345,065 B2 | 3/2008 | Gil et al. | |
| 7,507,398 B2 | 3/2009 | Rabinowitz et al. | |
| 7,524,812 B2 | 4/2009 | Ellis et al. | |
| 2001/0037104 A1 | 11/2001 | Zhang et al. | |
| 2002/0009454 A1 | 1/2002 | Boone | |
| 2002/0058656 A1 | 5/2002 | Ockert | |
| 2002/0090398 A1 | 7/2002 | Dunn | |
| 2002/0094998 A1 | 7/2002 | Burke et al. | |
| 2003/0022926 A1 | 1/2003 | Lavand'Homme | |
| 2003/0185873 A1 | 10/2003 | Chasin et al. | |

(Continued)

FOREIGN PATENT DOCUMENTS

| | | |
|---|---|---|
| WO | WO03005961 A2 | 1/2003 |
| WO | 2006011915 A1 | 2/2006 |

(Continued)

OTHER PUBLICATIONS

Rathnell et al. in a review in Anesthesia and Analgesia 2005; 101:S30-S43.*

(Continued)

*Primary Examiner* — Dennis Heyer
*Assistant Examiner* — Daniel M Podgorski
(74) *Attorney, Agent, or Firm* — Sorell Lenna & Schmidt LLP

(57) ABSTRACT

Effective treatments of acute pain for extended periods of time are provided. The treatments include the administration of one or more drug depots at or near a target site wherein the drug depots include an effective amount of clonidine formulated within a polyorthoester. By administration of one or more drug depots at or near the target site, one can relieve pain caused by diverse sources, including but not limited to spinal disc herniation (i.e. sciatica), spondilothesis, stenosis, discongenic back pain and joint pain, as well as pain that is incidental to surgery. In some embodiments, the relief can be for at least twenty-five days, at least fifty days, at least one hundred days or at least one hundred and thirty-five days.

19 Claims, 5 Drawing Sheets

(56) References Cited

U.S. PATENT DOCUMENTS

| | | |
|---|---|---|
| 2003/0229088 A1 | 12/2003 | Gil et al. |
| 2004/0028726 A1 | 2/2004 | Fischer et al. |
| 2004/0072799 A1 | 4/2004 | Li |
| 2004/0082540 A1 | 4/2004 | Hermida Ochoa |
| 2004/0101582 A1 | 5/2004 | Wolicki |
| 2004/0109893 A1* | 6/2004 | Chen et al. .............. 424/468 |
| 2004/0208917 A1 | 10/2004 | Fischer et al. |
| 2004/0214793 A1 | 10/2004 | Hermida Ochoa |
| 2004/0265364 A1 | 12/2004 | Ozturk et al. |
| 2005/0058696 A1 | 3/2005 | Donello et al. |
| 2005/0059744 A1 | 3/2005 | Donello et al. |
| 2005/0095277 A1 | 5/2005 | Ozturk et al. |
| 2005/0142163 A1 | 6/2005 | Hunter |
| 2005/0175709 A1 | 8/2005 | Baty |
| 2005/0177135 A1* | 8/2005 | Hildebrand et al. ....... 604/890.1 |
| 2005/0186261 A1 | 8/2005 | Avelar |
| 2005/0197293 A1 | 9/2005 | Mellis |
| 2005/0288620 A1 | 12/2005 | Shippert |
| 2006/0073182 A1 | 4/2006 | Wong |
| 2006/0074422 A1 | 4/2006 | Story |
| 2006/0148903 A1 | 7/2006 | Burch |
| 2006/0153815 A1 | 7/2006 | Seyda |
| 2006/0189944 A1 | 8/2006 | Campbell |
| 2006/0210604 A1 | 9/2006 | Dadey |
| 2006/0228391 A1 | 10/2006 | Seyedin |
| 2007/0021358 A1 | 1/2007 | Edelman |
| 2007/0066864 A1 | 3/2007 | Forde |
| 2007/0156180 A1 | 7/2007 | Jaax |
| 2007/0202074 A1 | 8/2007 | Shalaby |
| 2007/0243225 A1 | 10/2007 | McKay |
| 2007/0243228 A1 | 10/2007 | McKay |
| 2007/0253994 A1 | 11/2007 | Hildebrand |
| 2008/0009830 A1 | 1/2008 | Fujimoto |
| 2008/0091207 A1 | 4/2008 | Truckai |
| 2008/0152709 A1 | 6/2008 | Bortz |
| 2008/0171075 A1 | 7/2008 | Ozturk et al. |

FOREIGN PATENT DOCUMENTS

| | | |
|---|---|---|
| WO | 2006022611 A2 | 3/2006 |
| WO | 2006101540 A1 | 9/2006 |
| WO | 2008079868 A1 | 7/2008 |
| WO | 2009100441 A2 | 8/2009 |

OTHER PUBLICATIONS

Einmahl et al. in Investigative Ophthamology & Visual Science 42(3) 695-700 (2001).*

Kim et al. (International Journal of Pharmaceutics, 2005, 304, 165-177).*

International Search Report and Written Opinion for U.S. Application No. US/2009/040940 mailed on Dec. 14, 2009.

QLT, Inc., Atrigel Drug Delivery Platform, Jul. 2006.

* cited by examiner

CLONIDINE FORMULATION IN A POLYORTHOESTER CARRIER

This application claims the benefit of the filing date of U.S. Provisional Application No. 61/046,201 filed Apr. 18, 2008, entitled "Clonidine Formulations In A Biodegradable Polymer Carrier," and U.S. Provisional Application No. 61/046,213 filed Apr. 18, 2008, entitled "Medical Devices and Methods Including Polymers Having Biologically Active Agents Therein," both of which are hereby incorporated by reference thereto.

BACKGROUND

Proper pain control is of prime importance to anyone treating many different diseases or conditions. Proper pain relief imparts significant physiological and psychological benefits to the patient. Not only does effective pain relief mean a smoother more pleasant recovery (e.g., mood, sleep, quality of life, etc.) with earlier discharge from medical/surgical/outpatient facilities, but it may also reduce the progression of the acute pain state to a chronic pain syndrome (e.g., fibromyalgia, myalgia, etc.).

Pain serves an important biological function. It signals the presence of damage or disease within the body and is often accompanied by inflammation (redness, swelling, and/or burning). There are two categories of pain: acute pain and neuropathic pain. Acute pain refers to pain experienced when tissue is being damaged or is damaged. Acute pain serves at least two physiologically advantageous purposes. First, it warns of dangerous environmental stimuli (such as hot or sharp objects) by triggering reflexive responses that end contact with the dangerous stimuli. Second, if reflexive responses do not avoid dangerous environmental stimuli effectively, or tissue injury or infection otherwise results, acute pain facilitates recuperative behaviors. For example, acute pain associated with an injury or infection encourages an organism to protect the compromised area from further insult or use while the injury or infection heals. Once the dangerous environmental stimulus is removed, or the injury or infection has resolved, acute pain, having served its physiological purpose, ends. As contrasted to acute pain, in general, neuropathic pain serves no beneficial purpose. Neuropathic pain results when pain associated with an injury or infection continues in an area once the injury or infection has resolved.

There are many painful diseases or conditions that require proper pain and/or inflammation control, including but not limited to rheumatoid arthritis, osteoarthritis, a spinal disc herniation (i.e., sciatica), carpal/tarsal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, spondilothesis, stenosis, discogenic back pain, and joint pain or the like.

One particularly painful disease is sciatica. Sciatica is a chronic disease that often can be very debilitating and may take a terrible toll on those with the disease as well as their families, friends and caregivers. Sciatica is a very painful disease associated with the sciatic nerve which runs from the lower part of the spinal cord (the lumbar region), down the back of the leg and to the foot. Sciatica generally begins with a herniated disc, which later leads to local immune system activation. The herniated disc also may damage the nerve root by pinching or compressing it, leading to additional immune system activation in the area. There has been considerable interest in developing effective treatments for this painful disease, yet to date current treatments of sciatica are only partially effective.

Another particularly painful disease is spinal stenosis, where there is progressive constriction of the spinal canal and as it narrows, the nerve elements that reside within it become progressively more crowded. Eventually, the canal dimensions become sufficiently small so as to significantly compress the nerve elements and produce pain, weakness, sensory changes, clumsiness and other manifestations of nervous system dysfunction. The disease causes lower back pain, lower extremity pain, lower extremity weakness, limitation of mobility and the high disability rates that often afflict the elderly.

Spondylolisthesis is another painful disease. Spondylolisthesis is a displacement disorder of the lumbar or cervical spine, in which one vertebral body is forwardly displaced over another vertebral body. Spondylolisthesis may be caused by a traumatic event or by degeneration of the spine. At times, the displacement disorder is accompanied by or caused by a fracture or partial collapse of one or more vertebrae or degeneration of a disc in the spine. Patients who suffer from such conditions can experience moderate to severe distortion of the thoracic skeletal structure, diminished ability to bear loads, loss of mobility, extreme and debilitating pain, and oftentimes suffer neurological deficits.

One known class of pharmaceuticals to treat pain is opioids. This class of compounds is well-recognized as being among the most effective type of drugs for controlling pain, such as post-operative pain. Unfortunately, because opioids are administered systemically, the associated side effects raise significant concerns, including disabling the patient, depressing the respiratory system, constipation, and psychoactive effects such as sedation and euphoria, thereby instituting a hurdle to recovery and regained mobility. Consequently, physicians typically limit the administration of opioids to within the first twenty-four hours post-surgery. Thus, it would be preferable to use non-narcotic drugs that deliver direct, localized pain control at a surgical site.

One pharmaceutical that is known to the medical profession is clonidine, which is widely recognized as an antihypertensive agent that acts as an agonist on the alpha-2-adrenergic receptor and as a neural receptor agonist. In general, clonidine, also referred to as 2,6-dichloro-N-2-imidazolidinyldenebenzenamine ($C_9H_9Cl_2N_3$), may be represented by the following chemical structure:

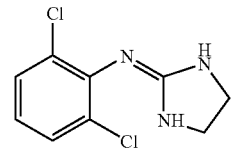 [SMILES: Clc1cccc(Cl)c1N=C1NCCN1]

However, to date it has not been widely appreciated as an effective local treatment for pain. Thus, there is a need to develop effective formulations of this compound for this application.

SUMMARY

Compositions and methods are provided comprising clonidine that are administered in order to treat acute pain. The compositions and methods may for example be used to treat pain due to a spinal disc herniation (i.e., sciatica), spondilothesis, stenosis, osteoarthritis, carpal/tarsal tunnel syndrome, tendonitis, temporomandibular joint disorder (TMJ) and discogenic back pain and joint pain, as well as pain that accompanies or follows surgery.

In one embodiment, an implantable drug depot useful for reducing, preventing or treating pain in a patient in need of such treatment is provided. The drug depot comprises a polyorthoester ("POE") and a therapeutically effective amount of clonidine. The drug depot is administered at a site to reduce, prevent or treat pain and the drug depot is capable of releasing clonidine in an amount between 0.005 and 1.0 mg per day for a period of 5 to 135 days. The drug depot may be capable of releasing clonidine in an amount between 0.01 and 0.1 mg per day for a period of 5 to 135 days. Clonidine may be present in an amount of about 0.1 to about 30 wt. % of the drug depot.

In another embodiment, a pharmaceutical formulation comprising clonidine, wherein the clonidine comprises from about 0.1 wt. % to about 30 wt. %, 1 wt. % to about 20 wt. % or about 5 wt. % to about 15 wt. % of the formulation, and a polyorthoester is provided. The pharmaceutical composition may for example, be part of a drug depot. The drug depot may: (i) consist of only the clonidine and the polyorthoester; or (ii) consist essentially of the clonidine and the polyorthoester; or (iii) comprise the clonidine, the polyorthoester and one or more other active ingredients, surfactants, excipients or other ingredients or combinations thereof. When there are other active ingredients, surfactants, excipients or other ingredients or combinations thereof in the formulation, in some embodiments these other compounds or combinations thereof comprise less than 20 wt. %, less than 19 wt. %, less than 18 wt. %, less than 17 wt. %, less than 16 wt. %, less than 15 wt. %, less than 14 wt. %, less than 13 wt. %, less than 12 wt. %, less than 11 wt. %, less than 10 wt. %, less than 9 wt. %, less than 8 wt. %, less than 7 wt. %, less than 6 wt. %, less than 5 wt. %, less than 4 wt. %, less than 3 wt. %, less than 2 wt. %, less than 1 wt. % or less than 0.5 wt. % of the drug depot. The drug depot is capable of releasing clonidine over a period of at least three days. The drug depot is capable of releasing: (i) a bolus dose of the clonidine at a site beneath the skin; and (ii) an effective amount of the clonidine over a period of at least fifty days.

According to another embodiment, there is an implantable drug depot for reducing, preventing or treating pain in a patient in need of such treatment, the implantable drug depot comprising clonidine in the form of a base in an amount of from about 0.1 wt. % to about 30 wt. % of the drug depot and a polyorthoester in an amount of at least 80 wt. % of the drug depot.

In still another embodiment, a method for treating acute pain is provided. The method comprises implanting a drug depot in an organism to reduce, prevent or treat pain. The drug depot comprises clonidine and a polyorthoester. Clonidine is present in an amount from about 0.1 wt. % to about 30 wt. %, about 1 wt. % to about 20 wt. % or about 5 wt. % to about 15 wt. % of the drug depot.

In still yet another embodiment, an implantable drug depot comprising a therapeutically effective amount of clonidine and a polyorthoester is provided. The drug depot is capable of releasing an initial bolus dose of the clonidine at a site beneath the skin of a patient, and the drug depot is capable of releasing a sustained release dose of an effective amount of the clonidine over a subsequent period of 5 to 135 days. The clonidine comprises about 1 wt. % to about 20 wt. % of the total wt. % of the drug depot and the polyorthoester comprises at least about 80 wt. % of the drug depot.

In another embodiment, a method of making an implantable drug depot is provided. The method comprises combining a polyorthoester and a therapeutically effective amount of clonidine and forming an implantable drug depot from the combination.

In various embodiments, clonidine may be in the form of a base. Alternatively, clonidine may be in the form of a salt. One example of a salt is a hydrochloric salt. Clonidine may also be in the form of a mixture of a hydrochloride salt and free base.

Clonidine in the various embodiments is capable of being released in an amount between 0.005 and 1.0 mg per day for a period of 5 to 135 days. The drug depot in the various embodiments is capable of releasing about 5% to about 100% of the clonidine relative to a total amount of the clonidine loaded in the drug depot over a period of 3 to 200 days after the drug depot is implanted in the organism.

The polyorthoester in the various embodiments may comprise about 70 wt. % to about 99.9 wt. % of the total wt. % of the drug depot. The polyorthoester is capable of degrading or degrades in 200 days or less after the drug depot is implanted at a site.

The drug depot in the various embodiments may further comprise one or more of poly(lactide-co-glycolide), polylactide, polyglycolide, D-lactide, D,L-lactide, L-lactide, D,L-lactide-co-ε-caprolactone, D,L-lactide-co-glycolide-co-ε-caprolactone or a combination thereof.

The drug depot in various embodiments may comprise a radiographic marker adapted to assist in radiographic imaging. The radiographic marker may comprise barium, bismuth, tantalum, tungsten, iodine, calcium phosphate, and/or metal beads.

The drug depot in various embodiments is capable of releasing between 0.05 microgram (ug) and 1 milligram (mg) per day of clonidine to reduce, prevent or treat pain.

The target site in the various embodiments comprises at least one muscle, ligament, tendon, cartilage, spinal disc, spinal foraminal space near the spinal nerve root, facet or synovial joint, or spinal canal.

The pain may be associated with hernia repair, orthopedic or spine surgery or a combination thereof. The surgery may be arthroscopic surgery, an excision of a mass, hernia repair, spinal fusion, thoracic, cervical, or lumbar surgery, pelvic surgery or a combination thereof.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1:
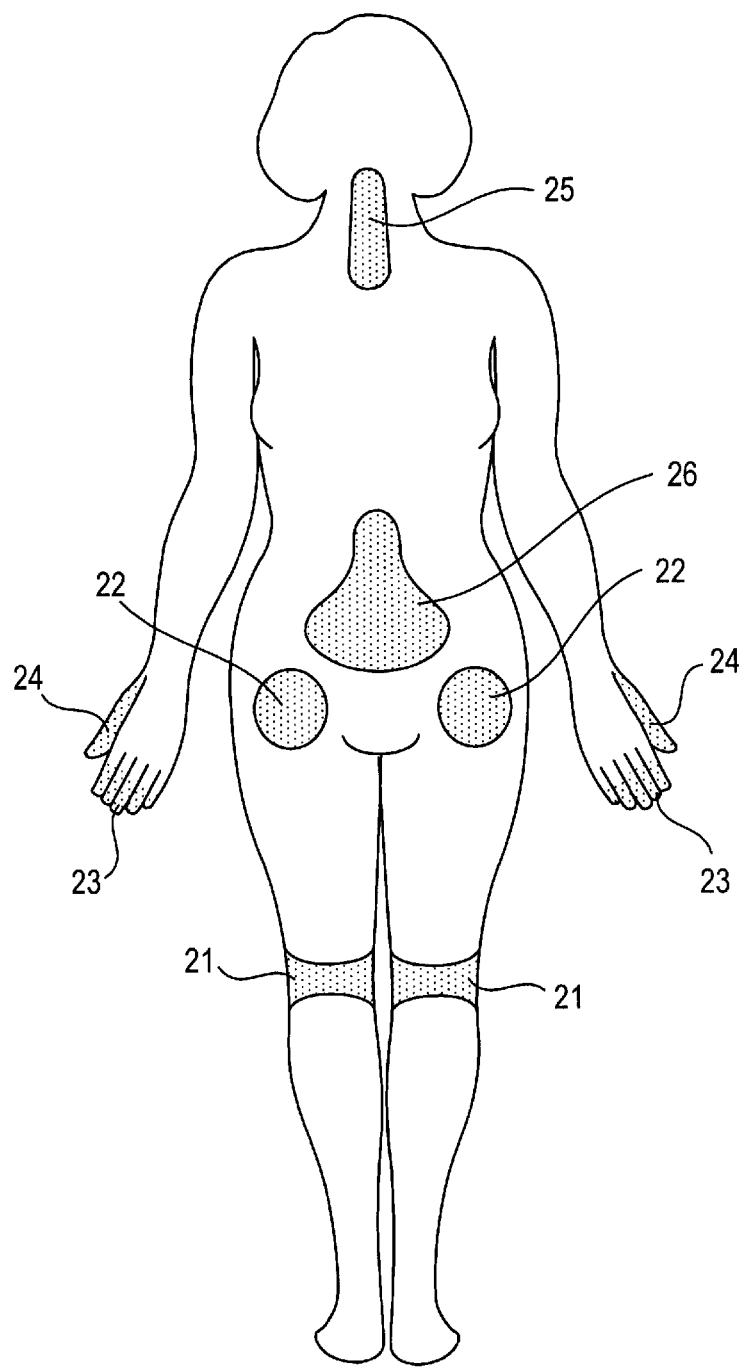
FIG. 1 illustrates a number of common locations within a patient that may be sites at which pain occurs and locations at which a drug depot containing clonidine and a polyorthoester can locally be administered thereto.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Definitions

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

A "drug depot" is the composition in which the clonidine is administered to the body. Thus, a drug depot may comprise a physical structure to facilitate implantation and retention in a desired site (e.g., a disc space, a spinal canal, a tissue of the patient, particularly at or near a site of chronic pain, etc.). The drug depot may also comprise the drug itself. The term "drug" as used herein is generally meant to refer to any substance that alters the physiology of a patient. The term "drug" may be used interchangeably herein with the terms "therapeutic agent," "therapeutically effective amount," and "active pharmaceutical ingredient" or "API." It will be understood that unless otherwise specified a "drug" formulation may include more than one therapeutic agent, wherein exemplary combinations of therapeutic agents include a combination of two or more drugs. The drug provides a concentration gradient of the therapeutic agent for delivery to the site. In various embodiments, the drug depot provides an optimal drug concentration gradient of the therapeutic agent at a distance of up to about 1 cm to about 5 cm from the administration site and comprises clonidine. A drug depot may also include a pump or pellet.

A "therapeutically effective amount" or "effective amount" is such that when administered, the drug results in alteration of the biological activity, such as, for example, inhibition of inflammation, reduction or alleviation of pain or spasticity, improvement in the condition through muscle relaxation, etc. The dosage administered to a patient can be as single or multiple doses depending upon a variety of factors, including the drug's administered pharmacokinetic properties, the route of administration, patient conditions and characteristics (sex, age, body weight, health, size, etc.), extent and duration of symptoms, concurrent treatments, frequency of treatment and the effect desired. In some embodiments, the formulation is designed for immediate release. In other embodiments, the formulation is designed for sustained release. In other embodiments, the formulation comprises one or more immediate release surfaces and one or more sustained release surfaces.

A "depot" includes but is not limited to capsules, microspheres, microparticles, microcapsules, microfibers particles, nanospheres, nanoparticles, coating, matrices, wafers, pills, pellets, emulsions, liposomes, micelles, gels, or other pharmaceutical delivery compositions or a combination thereof. Suitable materials for the depot are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof.

The term "biodegradable" includes that all or parts of the drug depot will degrade over time by the action of enzymes, by hydrolytic action and/or by other similar mechanisms in the human body. In various embodiments, "biodegradable" includes that the depot (e.g., microparticle, microsphere, etc.) can break down or degrade within the body to non-toxic components after or while a therapeutic agent has been or is being released. By "bioerodible" it is meant that the depot will erode or degrade over time due, at least in part, to contact with substances found in the surrounding tissue, fluids or by cellular action. By "bioabsorbable" it is meant that the depot will be broken down and absorbed within the human body, for example, by a cell or tissue. "Biocompatible" means that the depot will not cause substantial tissue irritation or necrosis at the target tissue site.

The phrases "sustained release" and "sustain release" (also referred to as extended release or controlled release) are used herein to refer to one or more therapeutic agent(s) that is introduced into the body of a human or other mammal and continuously or continually release an amount of one or more therapeutic agents over a predetermined time period and at a therapeutic level sufficient to achieve a desired therapeutic effect throughout the predetermined time period. Reference to a continuous or continual release is intended to encompass release that occurs as the result of biodegradation in vivo of the drug depot, or a matrix or component thereof, or as the result of metabolic transformation or dissolution of the therapeutic agent(s) or conjugates of therapeutic agent(s).

The phrase "immediate release" is used herein to refer to one or more therapeutic agent(s) that is introduced into the body and that is allowed to dissolve in or become absorbed at the location to which it is administered, with no intention of delaying or prolonging the dissolution or absorption of the drug.

The two types of formulations (sustain release and immediate release) may be used in conjunction. The sustained release and immediate release may be in one or more of the same depots. In various embodiments, the sustained release and immediate release may be part of separate depots. For example, a bolus or immediate release formulation of clonidine may be placed at or near the target site and a sustain release formulation may also be placed at or near the same site. Thus, even after the bolus becomes completely exhausted, the sustain release formulation would continue to provide the active ingredient for the intended tissue.

In various embodiments, the drug depot can be designed to cause an initial burst dose of therapeutic agent within the first twenty-four hours after implantation. "Initial burst" or "burst effect" or "bolus dose" refers to the release of therapeutic agent from the depot during the first twenty-four hours after the depot comes in contact with an aqueous fluid (e.g., synovial fluid, cerebral spinal fluid, etc.). The "burst effect" is believed to be due to the increased release of therapeutic agent from the depot. In alternative embodiments, the depot (e.g., gel) is designed to avoid this initial burst effect.

"Treating" or "treatment" of a disease or condition refers to executing a protocol that may include administering one or more drugs to a patient (human, other normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition. In addition, treating or treatment does not require complete alleviation of signs or symptoms, does not require a cure, and specifically includes protocols that have only a marginal effect on the patient.

"Localized" delivery includes delivery where one or more drugs are deposited within or near a tissue, for example, a nerve root of the nervous system or a region of the brain, or in close proximity (within about 0.1 cm, or preferably within about 10 cm, for example) thereto.

The term "mammal" refers to organisms from the taxonomy class "mammalian," including but not limited to humans, other primates such as chimpanzees, apes, orangutans and monkeys, rats, mice, cats, dogs, cows, horses, etc.

The phrase "pain management medication" includes one or more therapeutic agents that are administered to prevent, alleviate or remove pain entirely. These include anti-inflammatory agents, muscle relaxants, analgesics, anesthetics, narcotics, and so forth, and combinations thereof.

The phrase "release rate profile" refers to the percentage of active ingredient that is released over fixed units of time, e.g., mcg/hr, mcg/day, 10% per day for ten days, etc. As persons of ordinary skill know, a release rate profile may, but need not, be linear. By way of a non-limiting example, the drug depot may be a ribbon-like fiber that releases the clonidine over a period of time.

The term "solid" is intended to mean a rigid material, while, "semi-solid" is intended to mean a material that has some degree of flexibility, thereby allowing the depot to bend and conform to the surrounding tissue requirements.

"Targeted delivery system" provides delivery of one or more drugs depots, gels or depots dispersed in the gel having a quantity of therapeutic agent that can be deposited at or near the target site as needed for treatment of pain, inflammation or other disease or condition.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

The headings below are not meant to limit the disclosure in any way; embodiments under any one heading may be used in conjunction with embodiments under any other heading.

Clonidine

When referring to clonidine, the active ingredient may be in the salt form or the base form (e.g., free base). In various embodiments, if it is in the base form, it may be combined with a polymer such as a polyorthoester under conditions in which there is not severe polymer degradation. By way of a non limiting example, when formulating clonidine with a polyorthoester, it may be desirable to use the clonidine base formulation.

Further, clonidine may be in the salt form and one well-known commercially available salt for clonidine is its hydrochloride salt. Some other examples of potentially pharmaceutically acceptable salts include those salt-forming acids and bases that do not substantially increase the toxicity of a compound, such as, salts of alkali metals such as magnesium, potassium and ammonium, salts of mineral acids such as hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, and the like.

Clonidine may be administered with a muscle relaxant. Exemplary muscle relaxants include by way of example and not limitation, alcuronium chloride, atracurium bescylate, baclofen, carbamate, carbolonium, carisoprodol, chlorphenesin, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium, or combinations thereof.

The drug depot may comprise other therapeutic agents in addition to the clonidine as well. These therapeutic agents, in various embodiments, block the transcription or translation of TNF-α or other proteins in the inflammation cascade. Suitable therapeutic agents include, but are not limited to, integrin antagonists, alpha-4 beta-7 integrin antagonists, cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), HMGB-1 mAb (Critical Therapeutics Inc.), anti-IL2R antibodies (daclizumab, basilicimab), ABX (anti IL-8 antibodies), recombinant human IL-10, or HuMax IL-15 (anti-IL 15 antibodies).

Other suitable therapeutic agents include IL-1 inhibitors, such as Kineret® (anakinra) which is a recombinant, non-glycosylated form of the human interleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), bone morphogenic protein (BMP) type 2 and BMP-4 (inhibitors of caspase 8, a TNF-α activator), quinapril (an inhibitor of angiotensin II, which upregulates TNF-α), interferons such as IL-11 (which modulate TNF-α receptor expression), and aurin-tricarboxylic acid (which inhibits TNF-α), may also be useful as therapeutic agents for reducing inflammation. It is further contemplated that where desirable a pegylated form of the above may be used. Examples of still other therapeutic agents include NF kappa B inhibitors such as glucocorticoids, antioxidants, such as dithiocarbamate, and other compounds, such as, for example, sulfasalazine.

Examples of therapeutic agents suitable for use also include, but are not limited to an anti-inflammatory agent, an analgesic agent, or an osteoinductive growth factor or a combination thereof. Anti-inflammatory agents include, but are not limited to, apazone, celecoxib, diclofenac, diflunisal, enolic acids (piroxicam, meloxicam), etodolac, fenamates (mefenamic acid, meclofenamic acid), gold, ibuprofen, indomethacin, ketoprofen, ketorolac, nabumetone, naproxen, nimesulide, salicylates, sulfasalazine [2-hydroxy-5-[-4-[C2-pyridinylamino)sulfonyl]azo]benzoic acid, pentoxifylline, sulindac, tepoxalin or tolmetin; as well as antioxidants, such as dithiocarbamate, steroids, such as fluocinolone, cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable anabolic growth or anti-catabolic growth factors include, but are not limited to, a bone morphogenetic protein, a growth differentiation factor, a LIM mineralization protein, CDMP or progenitor cells or a combination thereof.

Suitable analgesic agents include, but are not limited to, acetaminophen, bupivacaine, lidocaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papavereturn, pentazocine, pethidine, phenoperidine, piritramide, dextropropoxyphene, remifentanil, tilidine, tramadol, codeine, dihydrocodeine, meptazinol, dezocine, eptazocine, flupirtine, amitriptyline, carbamazepine, gabapentin, pregabalin, or a combination thereof.

Clonidine may also be administered with non-active ingredients. These non-active ingredients may have multi-functional purposes including the carrying, stabilizing and controlling of the release of the therapeutic agent(s). The sustained release process, for example, may be by a solution-diffusion mechanism or it may be governed by an erosion-sustained process. Typically, the depot will be a solid or semi-solid formulation comprised of a biocompatible material that can be biodegradable.

Exemplary excipients that may be formulated with clonidine in addition to the biodegradable polymer include but are not limited to MgO (e.g., 1 wt. %), 5050 DLG 6E (Lakeshore Biomaterials, Inc.), 5050 DLG 1A (Lakeshore Biomaterials, Inc.), mPEG, TBO-Ac, mPEG, Span-65, Span-85, pluronic F127, TBO-Ac, sorbital, cyclodextrin, maltodextrin, pluronic F68, CaCl, 5050 7A and combinations thereof. In some embodiments, the excipients comprise from about 0.001 wt. % to about 50 wt. % of the formulation. In some embodiments, the excipients comprise from about 0.001 wt. % to about 40 wt. % of the formulation. In some embodiments, the excipients comprise from about 0.001 wt. % to about 30 wt. % of the formulation. In some embodiments, the excipients comprise from about 0.001 wt. % to about 20 wt. % of the formulation. In some embodiments, the excipients comprise from about 0.001 wt. % to about 10 wt. % of the formulation. In some embodiments, the excipients comprise from about 0.001 wt. % to about 50 wt. % of the formulation. In some embodiments, the excipients comprise from about 0.001 wt. % to about 2 wt. % of the formulation.

In various embodiments, the depot may comprise of a biodegradeable polyorthoester. The mechanism of the degradation process of the polyorthoester can be hydrolytical or enzymatical in nature, or both. In various embodiments, the degradation can occur either at the surface (heterogeneous or surface erosion) or uniformly throughout the drug delivery system depot (homogeneous or bulk erosion). Polyorthoester can be obtained from A.P. Pharma, Inc. (Redwood City, Calif.) or through the reaction of a bis(ketene acetal) such as 3,9-diethylidene-2,4,8,10-tetraoxospiro[5,5]undecane (DETOSU) with suitable combinations of diol(s) and/or polyol(s) such as 1,4-trans-cyclohexanedimethanol and 1,6-hexanediol or by any other chemical reaction that produces a polymer comprising orthoester moieties.

In some embodiments, the drug depot may not be completely biodegradable. For example, the drug depot may comprise polyorthoester and one of more of the following: polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. Typically, these types of drug depots may need to be removed after a certain amount of time.

In various embodiments, the depot may comprise a bio-erodable, a bioabsorbable, and/or a biodegradable biopolymer in addition to a polyorthoester that may provide immediate release, or sustained release of the clonidine. The biopolymer may also include one or more of the following biopolymers: poly (alpha-hydroxy acids), polylactide-co-glycolide (PLGA), polylactide (PLA), polyglycolide (PGA), D-lactide, D,L-lactide, L-lactide, D,L-lactide-co-ε-caprolactone, D,L-lactide-co-glycolide-co-ε-caprolactone, polyhydroxybutyrate, poly(glycolide-co-trimethylenecarbonate), poly(lactic acid-co-lysine), poly(lactide-co-urethane), poly (ester-co-amide), polyethylene glycol (PEG) conjugates of poly(alpha-hydroxy acids), polyaspirins, polyphosphazenes, polyanhydrides; polyketals, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, ε-caprolactone, dextrans, vinylpyrrolidone, polyvinyl alcohol (PVA), PVA-g-PLGA, PEGT-PBT copolymer (polyactive), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate), a POE or other biodegradeable polymer or combinations thereof. As persons of ordinary skill are aware, mPEG may be used as a plasticizer for a POE, but other polymers/excipients may be used to achieve the same effect. mPEG imparts malleability to the resulting formulations.

The depot may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide, sodium phosphate, magnesium oxide or magnesium carbonate; degradation/release modifiers; drug release adjusting agents; emulsifiers; preservatives such as benzalkonium chloride, chlorobutanol, phenylmercuric acetate and phenylmercuric nitrate, sodium bisulfate, sodium bisulfite, sodium thiosulfate, thimerosal, methylparaben, polyvinyl alcohol and phenylethyl alcohol; solubility adjusting agents; stabilizers; and/or cohesion modifiers. If the depot is to be placed in the spinal area, in various embodiments, the depot may comprise sterile preservative free material.

The depot can be of different sizes, shapes and configurations. There are several factors that can be taken into consideration in determining the size, shape and configuration of the drug depot. For example, both the size and shape may allow for ease in positioning the drug depot at the target tissue site that is selected as the implantation or injection site. In addition, the shape and size of the system should be selected so as to minimize or prevent the drug depot from moving after implantation or injection. In various embodiments, the drug depot can be shaped like a sphere, a pellet, a cylinder such as a rod or fiber, a flat surface such as a disc, film or sheet (e.g., ribbon-like) or the like. Flexibility may be a consideration so as to facilitate placement of the drug depot. In various embodiments, the drug depot has the shape of a pellet and has a length of from about 1 mm to 10 mm and a diameter of from about 0.5 mm to 5 mm.

Radiographic markers can be included on the drug depot to permit the user to position the depot accurately into the target site of the patient. These radiographic markers will also permit the user to track movement and degradation of the depot at the site over time. In this embodiment, the user may accurately position the depot in the site using any of the numerous diagnostic imaging procedures. Such diagnostic imaging procedures include, for example, X-ray imaging or fluoroscopy. Examples of such radiographic markers include, but are not limited to, barium, bismuth, tantalum, tungsten, iodine, calcium phosphate, and/or metal beads or particles. In various embodiments, the radiographic marker could be a spherical shape or a ring around the depot.

In some embodiments, the drug depot has pores that allow release of the drug from the depot. The drug depot will allow fluid in the depot to displace the drug. However, cell infiltration into the depot will be prevented by the size of the pores of the depot. In this way, in some embodiments, the depot will not function as a tissue scaffold and will not allow tissue growth. Rather, the drug depot will solely be utilized for drug delivery. Thus, the drug depot will have pore sizes less than 20 microns or 80 microns so as to prevent influx of cells so that the drug depot does not function as a tissue scaffold. In other embodiments, the depot has no pores and degrades based on the action of enzymes, by hydrolytic action and/or by other similar mechanisms in the human body. In other embodiments, the drug depot may have pore sizes above 80 microns to allow influx of cells and drug release and the drug depot may function, in this embodiment, as a tissue scaffold.

FIG. 1 illustrates a number of common locations within a patient that may be sites at which pain can occur and at which the drug depot may be administered. It will be recognized that the locations illustrated in FIG. 1 are merely exemplary of the many different locations at which pain can occur. For example, pain relief may be required at a patient's knees 21, hips 22, fingers 23, thumbs 24, neck 25, and spine 26.

Gel

In various embodiments, clonidine and polyorthoester are administered with or in a gel. The gel may have a pre-dosed viscosity in the range of about 1 to about 2,000 centipoise (cps), 1 to about 200 cps, or 1 to about 100 cps. After the gel is administered to the target site, the viscosity of the gel will increase and the gel will have a modulus of elasticity (Young's modulus) in the range of about $1 \times 10^2$ to about $6 \times 10^5$ dynes/cm$^2$, or $2 \times 10^4$ to about $5 \times 10^5$ dynes/cm$^2$, or $5 \times 10^4$ to about $5 \times 10^5$ dynes/cm$^2$.

The gel may be of any suitable type, as previously indicated, and should be sufficiently viscous so as to prevent the gel from migrating from the targeted delivery site once deployed; the gel should, in effect, "stick" or adhere to the targeted tissue site or conform to the target tissue space. The gel may, for example, solidify upon contact with the targeted tissue or after deployment from a targeted delivery system. The targeted delivery system may be, for example, a syringe, a catheter, needle or cannula or any other suitable device. The targeted delivery system may inject the gel into or on the targeted tissue site. The therapeutic agent may be mixed into the gel prior to the gel being deployed at the targeted tissue site. In various embodiments, the gel may be part of a two-component delivery system and when the two components are mixed, a chemical process is activated to form the gel and cause it to stick or to adhere to the target tissue.

The gel may harden or stiffen after delivery. Typically, hardening gel formulations may have a pre-dosed modulus of elasticity in the range of about $1 \times 10^2$ to about $3 \times 10^5$ dynes/cm$^2$, or $2 \times 10^2$ to about $2 \times 10^5$ dynes/cm$^2$, or $5 \times 10^2$ to about $1 \times 10^5$ dynes/cm$^2$. The post-dosed hardening gels (after delivery) may have a rubbery consistency and have a modulus of elasticity in the range of about $1 \times 10^4$ to about $2 \times 10^6$ dynes/cm$^2$, or $1 \times 10^5$ to about $7 \times 10^5$ dynes/cm$^2$, or $2 \times 10^5$ to about $5 \times 10^5$ dynes/cm$^2$.

If the gel includes clonidine and a polyorthoester, the polyorthoester concentration may affect the rate at which the gel hardens (e.g., a gel with a higher concentration of polymer may coagulate more quickly than gels having a lower concentration of polymer). In various embodiments, when the gel hardens, the resulting matrix is solid but is also able to conform to the irregular surface of the tissue (e.g., recesses and/or projections in bone).

The percentage of polyorthoester present in the gel may also affect the viscosity of the polymeric composition. For example, a composition having a higher percentage by weight of polymer is typically thicker and more viscous than a composition having a lower percentage by weight of polymer. A more viscous composition tends to flow more slowly. Therefore, a composition having a lower viscosity may be preferred in some instances. In some embodiments, the polyorthoester comprises 20 wt. % to 90 wt. % of the formulation.

In various embodiments, the molecular weight of the gel can be varied by many methods known in the art. The choice of method to vary molecular weight is typically determined by the composition of the gel (e.g., polymer, versus non-polymer). For example, in various embodiments, the degree of polymerization can be controlled by varying the amount of polymer initiators (e.g. benzoyl peroxide), organic solvents or activator (e.g. DMPT), crosslinking agents, polymerization agent, reaction time and/or by including chain transfer or chain terminating agents.

When the gel is designed to be a flowable gel, it can vary from low viscosity, similar to that of water, to high viscosity, similar to that of a paste, depending on the molecular weight and concentration of the polyorthoester used in the gel. The viscosity of the gel can be varied such that the composition can be applied to a patient's tissues by any convenient technique, for example, by brushing, dripping, injecting, or painting. Different viscosities of the gel will depend on the technique used to apply the composition.

In various embodiments, the gel has an inherent viscosity (abbreviated as "I.V." and units are in deciliters/gram), which is a measure of the gel's molecular weight and degradation time (e.g., a gel with a high inherent viscosity has a higher molecular weight and longer degradation time). Typically, a gel with a high molecular weight provides a stronger matrix and the matrix may take more time to degrade. In contrast, a gel with a low molecular weight may degrade more quickly and provides a softer matrix. In various embodiments, the gel has a molecular weight, as shown by the inherent viscosity, from about 0.10 dL/g to about 1.2 dL/g or from about 0.10 dL/g to about 0.40 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.50 dL/g, about 0.50 to about 0.70 dL/g, about 0.60 to about 0.80 dL/g, about 0.70 to about 0.90 dL/g, and about 0.80 to about 1.00 dL/g.

In various embodiments, the gel can have a viscosity of about 300 to about 5,000 centipoise (cp). In other embodiments, the gel can have a viscosity of from about 5 to about 300 cps, from about 10 cps to about 50 cps, or from about 15 cps to about 75 cps at room temperature. The gel may optionally have a viscosity enhancing agent such as, for example, hydroxypropyl cellulose, hydroxypropyl methylcellulose, hydroxyethyl methylcellulose, carboxymethylcellulose and salts thereof, Carbopol, poly-(hydroxyethylmethacrylate), poly-(methoxyethylmethacrylate), poly(methoxyethoxyethyl methacrylate), polymethylmethacrylate (PMMA), methylmethacrylate (MMA), gelatin, polyvinyl alcohols, propylene glycol, mPEG, PEG 200, PEG 300, PEG 400, PEG 500, PEG 600, PEG 700, PEG 800, PEG 900, PEG 1000, PEG 1450, PEG 3350, PEG 4500, PEG 8000 or combinations thereof.

Drug Delivery

It will be appreciated by those with skill in the art that the depot can be administered to the target site using a "cannula" or "needle" that can be a part of a drug delivery device e.g., a syringe, a gun drug delivery device, or any medical device suitable for the application of a drug to a targeted organ or anatomic region. The cannula or needle of the drug depot device is designed to cause minimal physical and psychological trauma to the patient.

Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style vital for accurate treatment of the patient depending on the site for implantation. Examples of tip styles include, for example, Trephine, Coumand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The dimensions of the hollow cannula or needle, among other things, will depend on the site for implantation. For example, the width of the epidural space is only about 3-5 mm for the thoracic region and about 5-7 mm for the lumbar region. Thus, the needle or cannula, in various embodiments, can be designed for these specific areas. In various embodiments, the cannula or needle may be inserted using a transforaminal approach in the spinal foramen space, for example, along an inflamed nerve root and the drug depot implanted at this site for treating the condition. Typically, the transforaminal approach involves approaching the intervertebral space through the intervertebral foramina.

Some examples of lengths of the cannula or needle may include, but are not limited to, from about 50 to 150 mm in length, for example, about 65 mm for epidural pediatric use, about 85 mm for a standard adult and about 110 mm for an obese adult patient. The thickness of the cannula or needle will also depend on the site of implantation. In various embodiments, the thickness includes, but is not limited to, from about 0.05 to about 1.655 (mm). The gauge of the cannula or needle may be the widest or smallest diameter or a diameter in between for insertion into a human or animal body. The widest diameter is typically about 14 gauge, while the smallest diameter is about 22 gauge. In various embodiments, the gauge of the needle or cannula is about 18 to about 22 gauge. In some embodiments, the needle or cannula may include two lumens: one for administering the drug depot and a second for administering a radiocontrast agent. This allows both to be administered without having to reposition the needle.

In various embodiments, like the drug depot and/or gel, the cannula or needle includes dose radiographic markers that indicate location at or near the site beneath the skin, so that the user may accurately position the depot at or near the site using any of the numerous diagnostic imaging procedures. Such diagnostic imaging procedures include, for example, X-ray imaging or fluoroscopy. Examples of such radiographic markers include, but are not limited to, barium, bismuth, tantalum, tungsten, iodine, gold, calcium, and/or metal beads or particles.

In various embodiments, the needle or cannula may include a transparent or translucent portion that can be visualizable by ultrasound, fluoroscopy, X-ray, or other imaging techniques. In such embodiments, the transparent or translucent portion may include a radiopaque material or ultrasound responsive topography that increases the contrast of the needle or cannula relative to the absence of the material or topography.

The drug depot, and/or medical device to administer the drug may be sterilizable. In various embodiments, one or more components of the drug depot, and/or medical device to administer the drug are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the drug depot is included in a gel.

Other methods may also be used to sterilize the depot and/or one or more components of the device, including, but not limited to, gas sterilization, such as, for example, with ethylene oxide or steam sterilization.

In various embodiments, a kit is provided that may include additional parts along with the drug depot and/or medical device combined together to be used to implant the drug depot. The kit may include the drug depot device in a first compartment. The second compartment may include a canister holding the drug depot and any other instruments needed for the localized drug delivery. A third compartment may include gloves, drapes, wound dressings and other procedural supplies for maintaining sterility of the implanting process, as well as an instruction booklet. A fourth compartment may include additional cannulas and/or needles. A fifth compartment may include an agent for radiographic imaging. Each tool may be separately packaged in a plastic pouch that is radiation sterilized. A cover of the kit may include illustrations of the implanting procedure and a clear plastic cover may be placed over the compartments to maintain sterility.

In various embodiments, a method for delivering a therapeutic agent into a site of a patient is provided, the method comprising inserting a cannula at or near a target tissue site and implanting the drug depot at the target site beneath the skin of the patient and brushing, dripping, injecting, or painting a gel in the target site to hold or have the drug depot adhere to the target site. In this way, unwanted migration of the drug depot away from the target site is reduced or eliminated.

In various embodiments, to administer the gel having the drug depot dispersed therein to the desired site, first the cannula or needle can be inserted through the skin and soft tissue down to the target tissue site and the gel administered at or near the target site. In those embodiments where the drug depot is separate from the gel, first the cannula or needle can be inserted through the skin and soft tissue down to the site of injection and one or more base layer(s) of gel can be administered to the target site. Following administration of the one or more base layer(s), the drug depot can be implanted on or in the base layer(s) so that the gel can hold the depot in place or reduce migration. If required, a subsequent layer or layers of gel can be applied on the drug depot to surround the depot and further hold it in place. Alternatively, the drug depot may be implanted first and then the gel placed around the drug depot to hold it in place. By using the gel, accurate and precise implantation of a drug depot can be accomplished with minimal physical and psychological trauma to the patient. The gel also avoids the need to suture the drug depot to the target site reducing physical and psychological trauma to the patient.

In various embodiments, when the target site comprises a spinal region, a portion of fluid (e.g., spinal fluid, etc.) can be withdrawn from the target site through the cannula or needle first and then the depot administered (e.g., placed, dripped, injected, or implanted, etc.). The target site will re-hydrate (e.g., replenishment of fluid) and this aqueous environment will cause the drug to be released from the depot.

Figure 2:
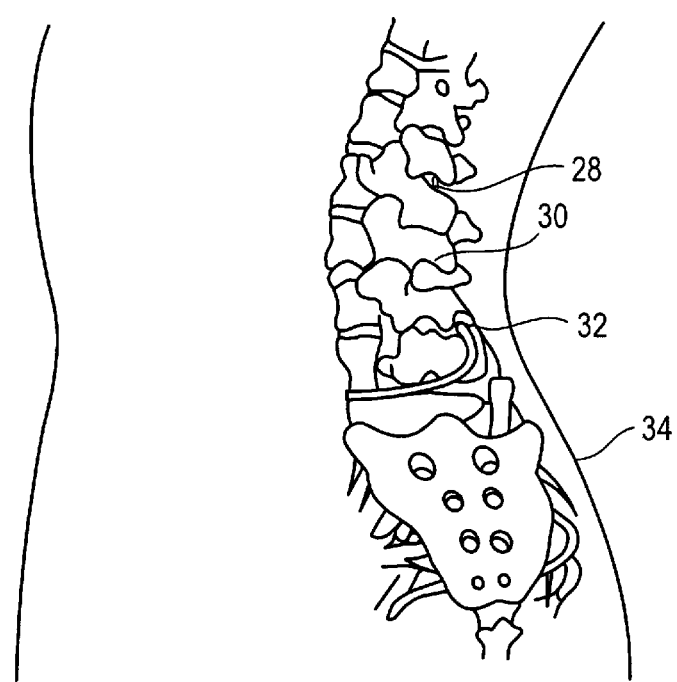
FIG. 2 illustrates a schematic dorsal view of the spine and sites at which a drug depot containing clonidine and a polyorthoester can locally be administered thereto.

One exemplary embodiment where the depot is suitable for use in treating spasticity (e.g., neuropathic pain management) and/or to treat conditions (e.g., sciatica) is illustrated in FIG. 2. Schematically shown in FIG. 2 is a dorsal view of the spine and sites where the drug depot may be inserted using a cannula or needle beneath the skin 34 to a spinal site 32 (e.g., spinal disc space, spinal canal, soft tissue surrounding the spine, nerve root, etc.) and one or more drug depots 28 and 32 are delivered to various sites along the spine. In this way, when several drug depots are to be implanted, they are implanted in a manner that optimizes location, accurate spacing, and drug distribution.

Although the spinal site is shown, as described above, the drug depot can be delivered to any site beneath the skin, including, but not limited to, at least one muscle, ligament, tendon, cartilage, spinal disc, spinal foraminal space, near the spinal nerve root, or spinal canal.

In some embodiments, it is preferable to administer an antagonist with a clonidine/POE formulation to counteract undesirable effects, for example the blood pressure decrease that can be caused by clonidine. Exemplary antagonists include but are not limited to phentolamine, yohimbine, tolazoline and piperoxane. Additionally, compounds such as 5-fluorodeoxyuridine (FUDR) and 3,4 dehydroprolene may also be included. These compounds may prevent or reduce glial and fibroblastic scar formation associated with some types of surgeries.

The formulations of the present application may be used as medicaments in the form of pharmaceutical preparations. The preparations may be formed in an administration with a suitable pharmaceutical carrier that may be solid or liquid and organic or inorganic, and placed in the appropriate form for parenteral or other administration as desired. As persons of ordinary skill are aware, known carriers include but are not limited to water, gelatine, lactose, starches, stearic acid, magnesium stearate, sicaryl alcohol, talc, vegetable oils, benzyl alcohols, gums, waxes, propylene glycol, polyalkylene glycols and other known carriers for medicaments.

Parenteral administration may additionally include, for example, an infusion pump that administers a pharmaceutical composition (e.g., analgesic and anti-inflammatory combination) through a catheter near the spine or one or more inflamed joints, an implantable mini-pump that can be inserted at or near the target site, an implantable controlled release device or sustained release delivery system that can release a certain amount of the drug per hour or in intermittent bolus doses. One example of a suitable pump for use is the SynchroMed® (Medtronic, Minneapolis, Minn.) pump. This pump has three sealed chambers. One contains an electronic module and battery. The second contains a peristaltic pump and drug reservoir. The third contains an inert gas that provides the pressure needed to force the pharmaceutical composition into the peristaltic pump. To fill the pump, the pharmaceutical composition is injected through the reservoir fill port to the expandable reservoir. The inert gas creates pressure on the reservoir, and the pressure forces the pharmaceutical composition through a filter and into the pump chamber. The pharmaceutical composition is then pumped out of the device from the pump chamber and into the catheter, which will direct it for deposit at the target site. The rate of delivery of pharmaceutical composition is controlled by a microprocessor. This allows the pump to be used to deliver similar or different amounts of pharmaceutical composition continuously, continually, at specific times, or at set intervals between deliveries.

In some embodiments, clonidine and polyorthoester formulations are suitable for parenteral administration. The term "parenteral" as used herein refers to modes of administration that bypass the gastrointestinal tract, and include for example, intravenous, intramuscular, continuous or intermittent infusion, intraperitoneal, intrasternal, subcutaneous, intra-operatively, intrathecally, intradiskally, peridiskally, epidurally, perispinally, intraarticular injection or combinations thereof. In some embodiments, the injection is intrathecal, which refers to an injection into the spinal canal (intrathecal space surrounding the spinal cord). An injection may also be into a muscle or other tissue.

Various techniques are available for forming at least a portion of a drug depot from the biocompatible polymer(s), therapeutic agent(s), and optional materials, including solution processing techniques and/or thermoplastic processing techniques. Where solution processing techniques are used, a solvent system is typically selected that contains one or more solvent species. The solvent system is generally a good solvent for at least one component of interest, for example, biocompatible polymer and/or therapeutic agent. The particular solvent species that make up the solvent system can also be selected based on other characteristics, including drying rate and surface tension.

Solution processing techniques include solvent casting techniques, spin coating techniques, web coating techniques, solvent spraying techniques, dipping techniques, techniques involving coating via mechanical suspension, including air suspension (e.g., fluidized coating), ink jet techniques and electrostatic techniques. Where appropriate, techniques such as those listed above can be repeated or combined to build up the depot to obtain the desired release rate and desired thickness.

In various embodiments, a solution containing a solvent and a biocompatible polymer are combined and placed in a mold of the desired size and shape. In this way, polymeric regions, including barrier layers, lubricious layers, and so forth can be formed. If desired, the solution can further comprise, one or more of the following: clonidine and other therapeutic agent(s) and other optional additives such as radiographic agent(s), etc. in dissolved or dispersed form. This results in a polymeric matrix region containing these species after solvent removal. In other embodiments, a solution containing solvent with dissolved or dispersed therapeutic agent is applied to a pre-existing polymeric region, which can be formed using a variety of techniques including solution processing and thermoplastic processing techniques, whereupon the therapeutic agent is imbibed into the polymeric region.

Thermoplastic processing techniques for forming a depot or portions thereof include molding techniques (for example, injection molding, rotational molding, and so forth), extrusion techniques (for example, extrusion, co-extrusion, multilayer extrusion, and so forth) and casting.

Thermoplastic processing in accordance with various embodiments comprises mixing or compounding, in one or more stages, the polyorthoester and one or more of the following: clonidine, optional additional therapeutic agent(s), radiographic agent(s), and so forth. The resulting mixture is then shaped into an implantable drug depot. The mixing and shaping operations may be performed using any of the conventional devices known in the art for such purposes.

During thermoplastic processing, there exists the potential for the therapeutic agent(s) to degrade, for example, due to elevated temperatures and/or mechanical shear that are associated with such processing. For example, clonidine may undergo substantial degradation under ordinary thermoplastic processing conditions. Hence, processing is preferably performed under modified conditions, which prevent the substantial degradation of the therapeutic agent(s). Although it is understood that some degradation may be unavoidable during thermoplastic processing, degradation is generally limited to 10% or less. Among the processing conditions that may be controlled during processing to avoid substantial degradation of the therapeutic agent(s) are temperature, applied shear rate, applied shear stress, residence time of the mixture containing the therapeutic agent, and the technique by which the polymeric material and the therapeutic agent(s) are mixed.

Mixing or compounding a polyorthoester with therapeutic agent(s) and any additional additives to form a substantially homogenous mixture thereof may be performed with any device known in the art and conventionally used for mixing polymeric materials with additives.

Where thermoplastic materials are employed, a polymer melt may be formed by heating the biocompatible polymer, which can be mixed with various additives (e.g., therapeutic agent(s), inactive ingredients, etc.) to form a mixture. A common way of doing so is to apply mechanical shear to a mixture of the biocompatible polymer(s) and additive(s). Devices in which the biocompatible polymer(s) and additive(s) may be mixed in this fashion include devices such as single screw extruders, twin screw extruders, banbury mixers, high-speed mixers, ross kettles, and so forth.

Any of the various additives and a polyorthoester may be premixed prior to a final thermoplastic mixing and shaping process, if desired (e.g., to prevent substantial degradation of the therapeutic agent among other reasons).

For example, in various embodiments, a polyorthoester is precompounded with a radiographic agent (e.g., radio-opacifying agent) under conditions of temperature and mechanical shear that would result in substantial degradation of the therapeutic agent, if it were present. This precompounded material is then mixed with therapeutic agent under conditions of lower temperature and mechanical shear, and the resulting mixture is shaped into the clonidine containing drug depot. Conversely, in another embodiment, the polyorthoester can be precompounded with the therapeutic agent under conditions of reduced temperature and mechanical shear. This precompounded material is then mixed with, for example, a radio-opacifying agent, also under conditions of reduced temperature and mechanical shear, and the resulting mixture is shaped into the drug depot.

The conditions used to achieve a mixture of the polyorthoester and therapeutic agent and other additives will depend on a number of factors including, for example, the additive(s) used, as well as the type of mixing device used.

In other embodiments, a polyorthoester and one or more therapeutic agents are premixed using non-thermoplastic techniques. For example, the polyorthoester can be dissolved in a solvent system containing one or more solvent species. Any desired agents (for example, a radio-opacifying agent, a therapeutic agent, or both radio-opacifying agent and therapeutic agent) can also be dissolved or dispersed in the solvents system. Solvent is then removed from the resulting solution/dispersion, forming a solid material. The resulting solid material can then be granulated for further thermoplastic processing (for example, extrusion) if desired.

As another example, the therapeutic agent can be dissolved or dispersed in a solvent system, which is then applied to a pre-existing drug depot (the pre-existing drug depot can be formed using a variety of techniques including solution and thermoplastic processing techniques, and it can comprise a variety of additives including a radio-opacifying agent and/or viscosity enhancing agent), whereupon the therapeutic agent is imbibed on or in the drug depot. As above, the resulting solid material can then be granulated for further processing, if desired.

Typically, an extrusion process may be used to form the drug depot comprising a polyorthoester, therapeutic agent(s) and radio-opacifying agent(s). Co-extrusion may also be employed, which is a shaping process that can be used to produce a drug depot comprising the same or different layers or regions (for example, a structure comprising one or more polymeric matrix layers or regions that have permeability to fluids to allow immediate and/or sustained drug release). Multi-region depots can also be formed by other processing and shaping techniques such as co-injection or sequential injection molding technology.

In various embodiments, the depot that may emerge from the thermoplastic processing (e.g., pellet) is cooled. Examples of cooling processes include air cooling and/or immersion in a cooling bath. In some embodiments, a water bath is used to cool the extruded depot. However, where a water-soluble therapeutic agent such as clonidine is used, the immersion time should be held to a minimum to avoid unnecessary loss of therapeutic agent into the bath.

In various embodiments, immediate removal of water or moisture by use of ambient or warm air jets after exiting the bath will also prevent re-crystallization of the drug on the depot surface, thus controlling or minimizing a high drug dose "initial burst" or "bolus dose" upon implantation or insertion if this is release profile is not desired.

In various embodiments, the drug depot can be prepared by mixing or spraying the drug with the polyorthoester and then molding the depot to the desired shape. In various embodiments, clonidine is used and mixed or sprayed with a polyorthoester, and the resulting depot may be formed by extrusion and dried.

In various embodiments, there is a pharmaceutical formulation comprising: clonidine, wherein the clonidine comprises from about 0.1 wt. % to about 30 wt. % of the formulation, and at least a polyorthoester. In some embodiments, the clonidine comprises from about 3 wt. % to about 20 wt. %, about 3 wt. % to about 18 wt. %, about 5 wt. % to about 15 wt. % or about 7.5 wt. % to about 12.5 wt. % of the formulation. By way of example, when using a 5%-15% clonidine hydrochloride composition combined with a polyothoester of approximately 80 kDalton that has a molar ratio of 267 grams/mole, the mole ratio of clonidine hydrochloride to polyorthoester would be from approximately 16-53. As another example, when using a 5%-15% clonidine base composition combined with a polyothoester of approximately 80 kDalton that has a molar mass of 230 grams/mole, the mole ratio of clondine base to polyorthoester would be approximately 18-61.

In some embodiments, the pharmaceutical formulation further comprises poly(lactic-co-glycolide) in addition to polyorthoester. The poly(lactic-co-glycolide) may comprise a mixture of polyglycolide (PGA) and polylactide and in some embodiments, in the mixture, there is more polylactide than polyglycolide. In various embodiments, there is 100% polylactide and 0% polyglycolide; 95% polylactide and 5% polyglycolide; 90% polylactide and 10% polyglycolide; 85% polylactide and 15% polyglycolide; 80% polylactide and 20% polyglycolide; 75% polylactide and 25% polyglycolide; 70% polylactide and 30% polyglycolide; 65% polylactide and 35% polyglycolide; 60% polylactide and 40% polyglycolide; 55% polylactide and 45% polyglycolide; 50% polylactide and 50% polyglycolide; 45% polylactide and 55% polyglycolide; 40% polylactide and 60% polyglycolide; 35% polylactide and 65% polyglycolide; 30% polylactide and 70% polyglycolide; 25% polylactide and 75% polyglycolide; 20% polylactide and 80% polyglycolide; 15% polylactide and 85% polyglycolide; 10% polylactide and 90% polyglycolide; 5% polylactide and 95% polyglycolide; and 0% polylactide and 100% polyglycolide.

In some embodiments where the pharmaceutical formulation further comprises poly(lactic-co-glycolide) in addition to polyorthoester, the poly(lactic-co-glycolide) includes at least 95% polylactide; at least 90% polylactide; at least 85% polylactide; at least 80% polylactide; at least 75% polylactide; at least 70% polylactide; at least 65% polylactide; at least 60% polylactide; at least 55%; at least 50% polylactide; at least 45% polylactide; at least 40% polylactide; at least 35% polylactide; at least 30% polylactide; at least 25% polylactide; at least 20% polylactide; at least 15% polylactide; at least 10% polylactide; or at least 5% polylactide; and the remainder of the poly(lactic-co-glycolide) is polyglycolide.

In various embodiments, the drug particle size is from about 5 to 30 micrometers, however, in various embodiments ranges from about 1 micron to 250 microns may be used. In some embodiments, the polyorthoester comprises at least 50 wt. %, at least 60 wt. %, at least 70 wt. %, at least 80 wt. % of the formulation, at least 85 wt. % of the formulation, at least 90 wt. % of the formulation, at least 95 wt. % of the formulation, at least 97 wt. % of the formulation.

In some embodiments, at least 75% of the particles have a size from about 10 micrometer to about 200 micrometers. In some embodiments, at least 85% of the particles have a size from about 10 micrometer to about 200 micrometers. In some embodiments, at least 95% of the particles have a size from about 10 micrometer to about 200 micrometers. In some embodiments, all of the particles have a size from about 10 micrometer to about 200 micrometers.

In some embodiments, at least 75% of the particles have a size from about 20 micrometer to about 180 micrometers. In some embodiments, at least 85% of the particles have a size from about 20 micrometers to about 180 micrometers. In some embodiments, at least 95% of the particles have a size from about 20 micrometer to about 180 micrometers. In some embodiments, all of the particles have a size from about 20 micrometer to about 180 micrometers.

In some embodiments, there is a pharmaceutical formulation comprising: clonidine, wherein the clonidine is in the form of a hydrochloride salt, and comprises from about 0.1 wt. % to about 30 wt. % of the formulation, and at least a polyorthoester, wherein the polyorthoester comprises at least 70 wt. % of said formulation. In some embodiments, there is a pharmaceutical formulation comprising: clonidine, wherein a portion of the clonidine is in the form of a hydrochloride salt, and a portion is in the form of clonidine base, and the mixture comprises about 0.1 wt. % to about 30 wt. % of the formulation, and at least a polyorthoester, wherein the polyorthoester comprises at least 70 wt. % of said formulation.

In some embodiments, there are methods for treating acute pain. These methods comprise: administering a pharmaceutical composition to an organism, wherein said pharmaceutical composition comprises from about 0.1 wt. % to about 30 wt. % of the formulation, and at least a polyorthoester. In some embodiments, the loading is from about 5 wt. % to about 10 wt. %. In some embodiments, the loading is from about 10 wt. % to about 20 wt. %.

In some embodiments, there is a higher loading of clonidine, e.g., at least 20 wt. %, at least 30 wt. %, at least 40 wt. %, at least 50 wt. %, at least 60 wt. %, at least 70 wt. %, at least 80 wt. %, or at least 90 wt. %.

A strategy of triangulation may be effective when administering these pharmaceutical formulations. Thus, a plurality (at least two, at least three, at least four, at least five, at least six, at least seven, etc.) of drug depots comprising the pharmaceutical formulations may be placed around the target tissue site (also known as the pain generator or pain generation site) such that the target tissue site falls within a region that is either between the formulations when there are two, or within an area whose perimeter is defined by a set of plurality of formulations.

In some embodiments, the formulations are slightly rigid with varying length, widths, diameters, etc. For example, certain formulations may have a diameter of 0.50 mm and a length of 4 mm. It should be noted that particle size may be altered by techniques such as mortar and pestel, grinding, jet-drying or jet milling.

In some embodiments, clonidine is released at a rate of 2-3 μg per day for a period of at least three days. In some embodiments, this release rate continues for, at least ten days, at least fifteen days, at least twenty-five days, at least fifty days, at least ninety days, at least one hundred days, at least one-hundred and thirty-five days, at least one-hundred and fifty days, or at least one hundred and eighty days. For some embodiments, 300-425 micrograms of clonidine as formulated with a polyorthoester are implanted into a person at or near a target tissue site. If clonidine is implanted at multiple sites that triangulate the target site, then in some embodiments, the total amount of clonidine at each site is a fraction of the total 300-425 micrograms. For example, one may implant a single dose of 324 micrograms at one site, or two separate doses of 162 micrograms at two sites, or three separate doses of 108 micrograms at three sites that triangulate the tissue site. It is important to limit the total dosage to an amount less than that which would be harmful to the organism. However, in some embodiments, although when there are a plurality of sites each site may contain less than the total dose that might have been administered in a single application, it is important to remember that each site will independent have a release profile, and the polyorthoester concentration should be adjusted accordingly to ensure that the sustain release occurs over sufficient time.

The dosage may be from approximately 0.0005 to approximately 960 μg/day. Additional dosages of clonidine include from approximately 0.0005 to approximately 900 μg/day; approximately 0.0005 to approximately 500 μg/day; approximately 0.0005 to approximately 250 μg/day; approximately 0.0005 to approximately 100 μg/day; approximately 0.0005 to approximately 75 μg/day; approximately 0.001 to approximately 70 μg/day; approximately 0.001 to approximately 65 μg/day; approximately 0.001 to approximately 60 μg/day; approximately 0.001 to approximately 55 μg/day; approximately 0.001 to approximately 50 μg/day; approximately 0.001 to approximately 45 μg/day; approximately 0.001 to approximately 40 μg/day; approximately 0.001 to approximately 35 μg/day; approximately 0.0025 to approximately 30 μg/day; approximately 0.0025 to approximately 25 μg/day; approximately 0.0025 to approximately 20 μg/day; approximately 0.0025 to approximately 15 μg/day; approximately 0.0025 to approximately 10 μg/day; approximately 0.0025 to approximately 5 μg/day; and approximately 0.0025 to approximately 2.5 μg/day. In another embodiment, the dosage of clonidine is from approximately 0.005 to approximately 15 μg/day. In another embodiment, the dosage of clonidine is from approximately 0.005 to approximately 10 μg/day. In another embodiment, the dosage of clonidine is from approximately 0.005 to approximately 5 μg/day. In another embodiment, the dosage of clonidine is from approximately 0.005 to 2.5 μg/day. In some embodiments, the amount of clonidine is between 40 and 600 μg/day. In some embodiments, the amount of clonidine is between 200 and 400 μg/day.

In one exemplary dosing regiment, a rat may be provided with sufficient clonidine in a biodegradable POE polymer to provide sustained release of 0.240 μg/day clonidine for 135 days. The total amount of clonidine that is administered over this time period would be approximately 32.4 μg. In another exemplary dosing regiment, a human is provided with sufficient clonidine in a biodegradable POE polymer to provide sustained release of 2.4 μg/day clonidine for 135 days. The total amount of clonidine that is administered over this time period would be approximately 324 μg.

When using a plurality of pellets, the pellet number is based on the amount of drug loading into a pellet of appropriate size (i.e., 0.5 mm diameter×4 mm length) and how much drug is needed (e.g., approximately 325 μg clonidine (3 pellets)). In some embodiments, there is a POE polymer that releases a bolus amount of compound over the first few (~5) days before it settles down and releases 0.025 mg/day for 135 days.

In some embodiments, the polymer depots of present invention enable one to provide efficacy of the active ingredient that is equivalent to subcutaneous injections that deliver more than 2.5 times as much drug.

Having now generally described the invention, the same may be more readily understood through the following reference to the following examples, which are provided by way of illustration and are not intended to limit the present invention unless specified.

EXAMPLES

The examples below show certain particularly advantageous results wherein the initial burst is not too large (i.e., not more than 7% of the load drug in the first five days) and the daily dose is approximately 2.4 μg/day±0.5 μg/day for 135 days. The figures demonstrate that the formulations of the present invention provide advantageous results.

Figure 3:
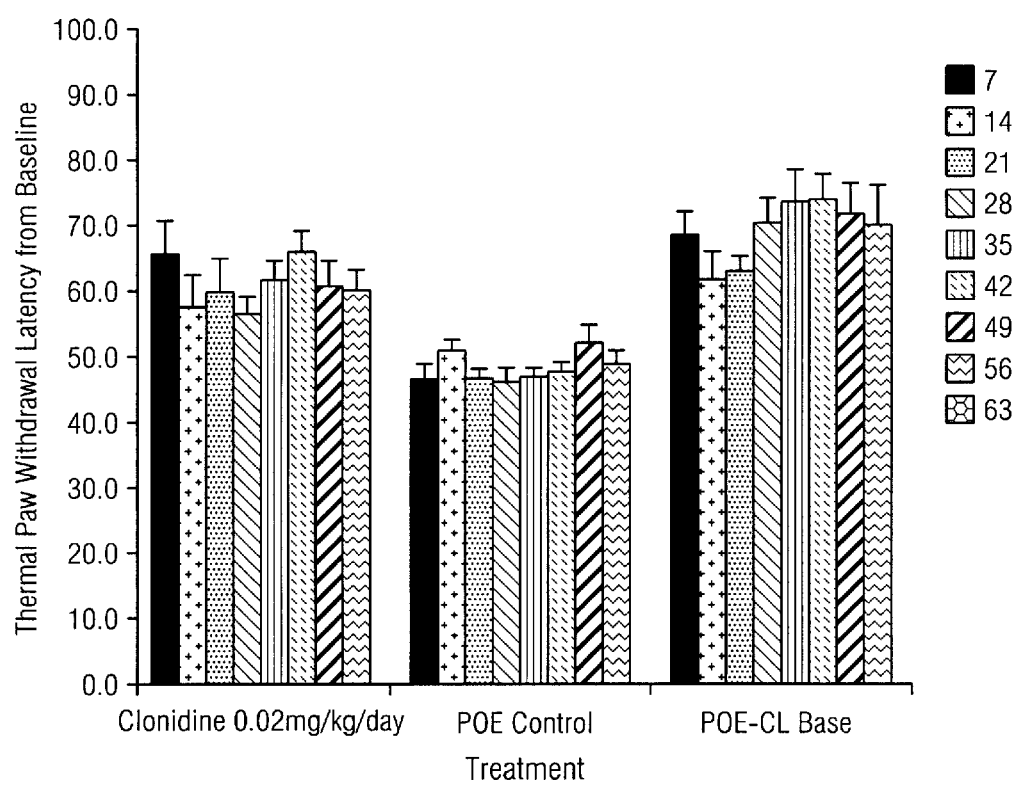
FIG. 3 is a graphic representation of the thermal paw withdrawal latency as a percentage from baseline for the following administrations: clonidine ("CL") 0.02 mg/kg/day subcutaneously, POE Control and POE CL-Base at 7 days, 14 days, 21 days, 28 days, 35 days, 42 days, 49 days, 56 days and 63 days. "POE" refers to polyorthoester. "CL-Base" refers to clonidine in its base form.
Figure 4:
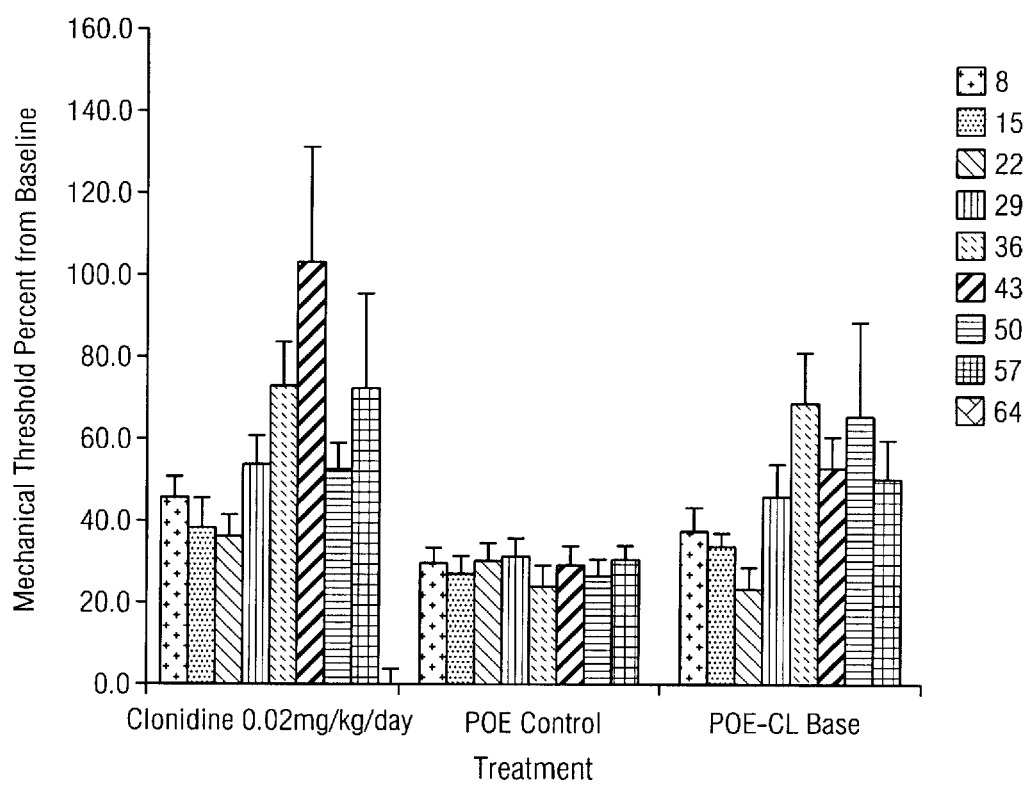
FIG. 4 is a graphic representation of the mechanical threshold as a percentage from baseline for the following administrations: clonidine 0.02 mg/kg/day subcutaneously, POE Control and POE CL-Base at 8 days, 15 days, 22 days, 29 days, 36 days, 43 days, 50 days, 57 days and 64 days.

A 2-month chronic constriction injury (CCI) model of neuropathic pain was used to evaluate a formulation of clonidine encapsulated in a POE polymer, a POE control polymer and clonidine given subcutaneously (SC). The 3 compositions/formulations are provided in Table 3 below and were evaluated for reducing pain-associated behaviors: thermal paw withdrawal latency was evaluated at baseline 7, 14, 21, 28, 35, 42, 49, 56 and 64 days post-operatively, while mechanical threshold was evaluated at 8, 15, 22, 29, 36, 43, 50, 57 and 64 days post-operatively. Bar graphs depicting the results of theses tests are shown in FIGS. 3 and 4.

Example 1

In-Vitro Release of Clonidine and Polyorthoester Formulations

The inventors prepared a number of clonidine/polyorthoester formulations in which they varied the polymer type, drug load and pellet size. The formulations were prepared according to the following procedures:

Materials: A polyorthoester having a molecular weight of 133 kDaltons was synthesized by combining a stoichiometric mixture of 3,9-diethylidene-2,4,8,10-tetraoxospiro[5,5]undecane (DETOSU) with a mixture of diols including trans-1,4-cyclohexanedimethanol (54 mole %), 1,6-hexanediol (45 mole %) and diethyl-tartrate (1 mole %). Clonidine HCl was purchased from Spectrum Chemicals (Gardena, Calif.). Methanol and acetone were also purchased from Sigma-Aldrich.

Methods: Preparation of Polyorthoester: The following compositions were used to prepare a polyothoester: DETOSU at 34.9998 g (164.90 mmole), Trans-cyclohexanedimethanol at 12.5898 g (87.30 mmole), 1,6-hexanediol at 8.5965 g (72.75 mmole), Diethyltartrate at 0.3333 g (1.62 mmole), Para-toluenesulfonicacid at 2325 μl of a 1% (w/v) solution in tetrahydrofuran (THF) and 315 ml of Tetrahydrofuran. In particular, a 1000 ml round bottomed flask was pyro-cleaned, washed with soap and water, then rinsed with acetone, isopropanol, 0.1N NaOH and deionized water, and then oven-dried. All spatulas to be used for preparing the polymer were washed and dried in the oven for at least 2 hours. A small glass beaker was also washed and dried in the oven. All of the reactants were weighed in a beaker. In a $N_2$ glove box, DETOSU was first weighed into the beaker followed by the diols. 200 ml of THF was then added to dissolve the solids and this solution was poured into the round bottomed flask. The rest of the THF was then added to the beaker again and then into the flask. The solution was allowed to stir for 30 minutes. A 1% PTSA catalyst was then added to the solution at which point the solution exothermed vigorously and became very thick. The stirring was then stopped and the solution was allowed to sit overnight. An IR scan of a sample of the polymer solution was taken the next day and it showed that the polymerization was complete (there was a minor peak at 3501 cm$^{-1}$ but that was due to the thickness of the sample on the IR plate).

A blender was washed and dried in the oven for at least 8 hours. A tweezer was also dried. In the $N_2$ glove box, ~500 ml of anhydrous methanol was added to the blender. Four (4) drops of triethylamine were then added to the waring blender. The polymer solution was then slowly poured into a methanol solution. The polymer precipitated out easily. The precipitated polymer was then re-dissolved in minimal THF and poured in fresh methanol. The polymer precipitated again and was then put in a mylar boat and dried in the vacuum oven at full vacuum and 50° C. for two days. The POE polymer was then transferred to a dried jar.

Methods: Preparation of Spray Dried Clonidine HCl: Clonidine HCl was dissolved in methanol to yield a 12% (w/w) solution. The solution was spray dried in a Buchi B-290 Mini Spray Dryer (Buchi Laboratorium AG, Switzerland) using a 120 kHz Sono-Tek ultrasonic nozzle (Sono-Tek Corp., Milton, N.Y.). The processing parameters were set as follows: inlet temp. (70° C.), aspirator (80%), nitrogen inlet (50 mm), spray flow rate (80 mL/hr) and ultrasonic generator (0.8 watts). The spray dried powder was collected and dried for additional 24 hours at 70° C. and 15 mmHg vacuum.

Methods: Preparation of Melt Extruded Rods: Several formulations (as described in Table 1 below) having clonidine HCl drug loadings of 5% (w/w), 10% (w/w) and 20% (w/w) were prepared for melt extrusion with POE. Each formulation contained POE polymer ground into powder using a Retsch (Retsch GmbH, Germany) rotor mill with an 80 micrometer sieve filter and spray dried clonidine HCl as described above. All formulations were dry mixed with a spatula prior to being fed into a Haake Mini-Lab twin screw extruder (Thermo Fischer Scientific, Waltham, Mass.) set at 120° C. and 30 RPM. The rods were extruded out of a 0.75 mm diameter die and pulled by hand to obtain a final diameter of ~0.7-0.8 mm.

The rods were then cut with a razor blade to lengths of 0.75 mm and 1.5 mm depending on the corresponding drug loadings of 20%, 10% and 5%. Pellets from each formulation were placed in 20 mL scintillation vials for drug elution testing. In-vitro elution studies were carried out at 37° C. in phosphate-buffered saline (PBS, pH 7.4). In particular, the pellets were incubated in 5 mL of phosphate buffered saline pH 7.4 (Hyclone, 0.0067M) at 37° C. under mild agitation. At pre-selected times, the buffer was removed for analysis and replaced with fresh buffer medium. The drug content was quantified at 226 nm by a Molecular Devices SpectraMax M2 (Sunnyvale, Calif.) plate reader.

TABLE 1

| Notebook ID | Polymer Type | Drug Load (Wt %) | Excipient | Pellet Size (L × Dia; mm) or Description | Processing |
|---|---|---|---|---|---|
| 13335-73-1 | POE 58 | 10 | N/A | 1.5 × 0.75 | Melt extrusion |
| 13335-73-2 | POE 58 | 20 | N/A | 0.75 × 0.75 | Melt extrusion |
| 13335-73-3 | POE 60 | 10 | N/A | 1.5 × 0.75 | Melt extrusion |
| 13335-73-4 | POE 60 | 20 | N/A | 0.75 × 0.75 | Melt extrusion |
| 13699-1-2 | POE 58 | 10 | N/A | 4-1.5 × 0.75 | Melt extrusion |
| 13699-1-3 | POE 58 | 20 | N/A | 1-0.75 × 0.75 | Melt extrusion |
| 13395-17-1 | POE (13166-75) | 5 | N/A | 1.5 × 1.5 | Melt extrusion |
| 13395-17-2 | POE (13166-77) | 5 | N/A | 1.5 × 1.5 | Melt extrusion |

Figure 5:
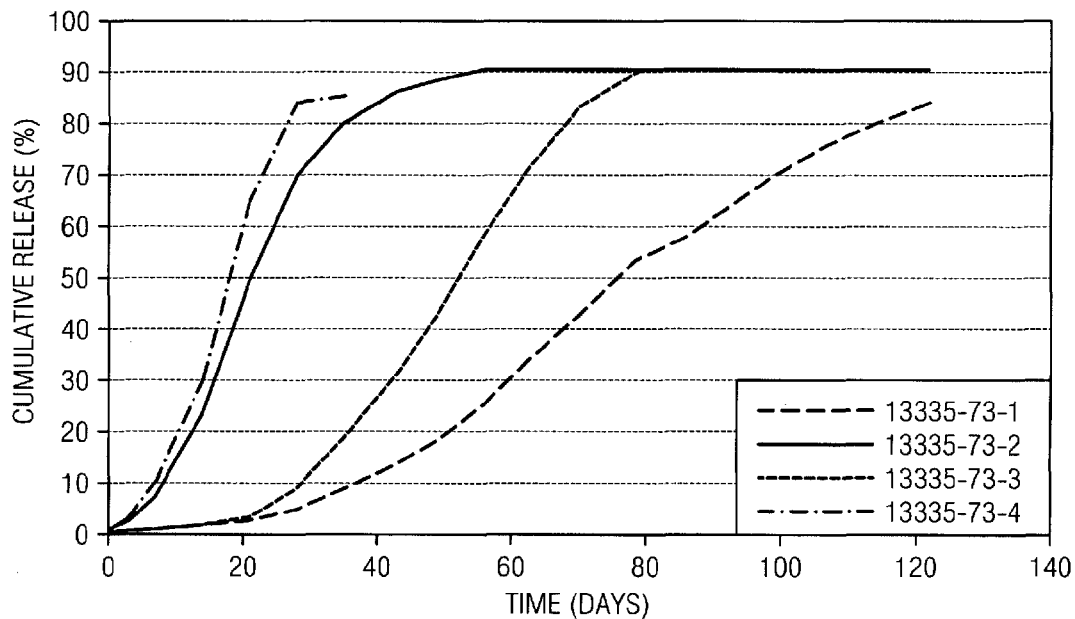
FIG. 5 is a graphic representation of the cumulative release percentage of clonidine for certain formulations.
Figure 6:
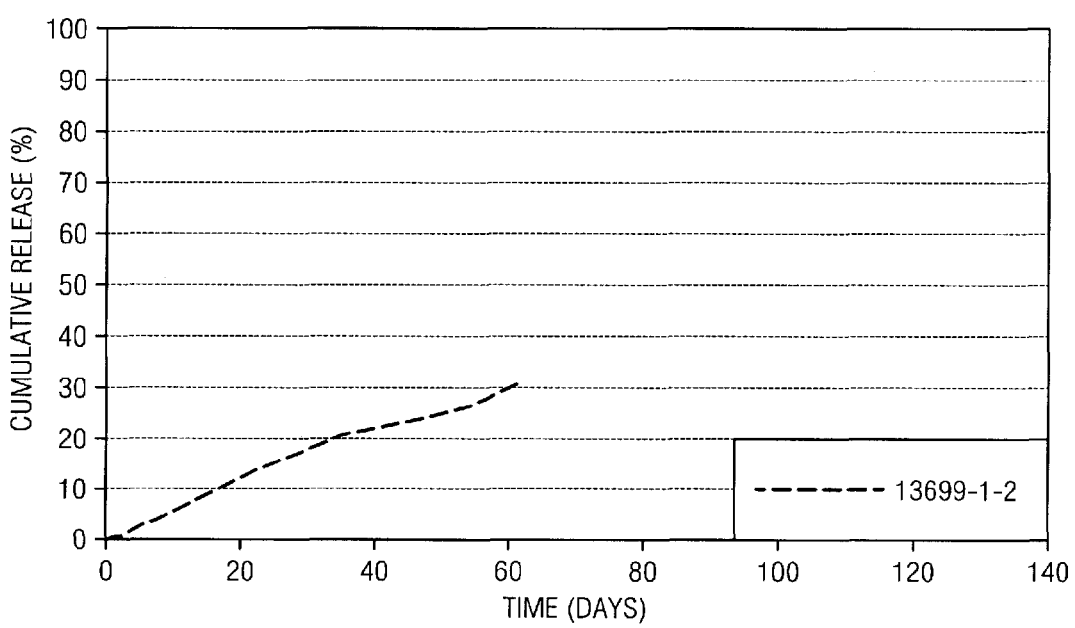
FIG. 6 is a graphic representation of the cumulative release percentage of clonidine for one formulation.

These formulations from Table 1 were analyzed in terms of their in vitro release in which the number of micrograms released was measured, as well as the cumulative percentage release of clonidine. FIGS. 5 and 6 show the percentage cumulative release of clonidine over time for the formulations described in Table 1. As is readily apparent from FIG. 5, the formulations with a higher drug load steadily released clonidine for about the first 5-10 days and then clonidine was released at a more rapid rate during the next 20 days. Formulation 13335-73-1 steadily released clonidine over a 120 day period. As is apparent from FIG. 6, formulation 13699-1-2 steadily released clonidine over a 60 day period.

Example 2

Implantation of Pellets

The inventors evaluated the efficacy of a five month Clonidine/Polyorthoester Drug Depot in the Rat Chronic Constriction Injury Model. The animal model was the Bennett Model (Wistar rat). The purpose: to determine whether a five month polyorthoester clonidine-eluting depot can improve pain associated behavioral responses in a rat model of neuropathic pain.

Experimental Design: Four loose chromic gut ligatures, 1 mm apart, were tied around the common sciatic nerve at mid-thigh. Each animal received treatment of test or a controlled article according to the dosing described in Table 2.

TABLE 2

| Group Number | Treatment | Dose | Formulation Group | Comments |
|---|---|---|---|---|
| 1 | Clonidine | 0.02 mg/kg SC | | Clonidine control |
| 2 | POE | 0% | | 5 pellets (1.5 mm × 0.7 mm) |
| 3 | POE | 10 and 20% | | clonidine-base; 5 pellets (1.20% @ 0.7 mm$^2$; 4.10% @ 1.5 mm × 0.7 mm) |

The inventors have conducted the present study for a period of 64 days and have employed the following two tests: (1) the Hargreaves test; and (2) the von Frey test. The Hargreaves Tests of Thermal Hyperalgesia were conducted on days 7, 14, 21, 28, 35, 42, 49, 56 and 63. The von Frey monofilament test of mechanical allodynia (performed the day following thermal testing) were conducted on days 8, 15, 22, 29, 36, 43, 50, 57 and 64. The results of these tests are summarized in FIGS. 3 and 4 and show the efficacy of clonidine at the recited time periods.

The pain behavioral response (measured as a percentage of baseline) for thermal hyperalgesia (FIG. 3) indicates that clonidine delivered subcutaneously at 0.02 mg/kg/day consistently reduced the behavioral response when compared to the unloaded polyorthoester depot (POE Control). The clonidine-loaded polyorthoester depot was able to reduce pain behavioral responses when compared to the unloaded depot; although, each formulation experienced a slight drop in efficacy at some point after the initial burst of drug at implantation. The pain behavioral response (measured as a percentage of baseline) for mechanical allodynia indicates that clonidine delivered subcutaneously at 0.02 mg/kg/day reduced the behavioral response when compared to the unloaded polyorthoester depot (POE Control).

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. An implantable drug depot . . . is a gel having an inherent viscosity of about 0.10 dL/g to about 1.2 dL/g, and the drug depot further comprises an excipient comprising mPEG in an amount from about 0.001 wt. % to about 2 wt. % of the drug depot.

2. An implantable drug depot according to claim 1, wherein said polyorthoester is capable of degrading in 200 days or less after the drug depot is administered at the site.

3. An implantable drug depot according to claim 1, wherein said clonidine is released in an amount between 0.01 and 0.1 mg per day for a period of 5 to 135 days at the site.

4. An implantable drug depot according to claim 1, wherein said clonidine is present in an amount of about 1 to about 10 wt. % of the drug depot and said polyorthoester is present in an amount of about 90 to about 99 wt. % of the drug depot.

5. An implantable drug depot . . . is a gel having an inherent viscosity of about 0.10 dL/g to about 1.2 dL/g, and the drug depot further comprises an excipient comprising mPEG in an amount from about 0.001 wt. % to about 2 wt. % of the drug depot.

6. An implantable drug depot according to claim 5, wherein said clonidine comprises from about 10 wt. % to about 15 wt. % of the drug depot.

7. An implantable drug depot according to claim 5, wherein said clonidine is released in an amount between 0.005 and 1.0 mg per day for a period of 5 to 135 days.

8. An implantable drug depot according to claim 5, wherein said polyorthoester comprises at least 70 wt. % of the drug depot.

9. An implantable drug depot according to claim 5, further comprising one or more of poly(lactide-co-glycolide), poly-lactide, polyglycolide, D-lactide, D,L-lactide, L-lactide, D,L-lactide-co-ε-caprolactone, D,L-lactide-co-glycolide-co-ε-caprolactone or a combination thereof.

10. An implantable drug depot according to claim 5, wherein said clonidine is in the form of a hydrochloric salt or a mixture of hydrochloride salt and free base.

11. An implantable drug depot according to claim 5, wherein the drug depot releases an effective amount of said clonidine over a period of at least fifty days.

12. An implantable drug depot comprising: (i) a therapeutically effective amount of clonidine, the clonidine loaded in the drug depot in an amount of from about 1 wt. % to about 20 wt. % based on the total weight of the drug depot and the clonidine having a particle size range of from about 1 micrometers to about 200 micrometers; and (ii) a polyorthoester; wherein the drug depot has a region that releases an initial burst of clonidine in an amount of not more than 7% of the clonidine loaded in the depot within five days at a site beneath the skin of a patient, and the drug depot is capable of releasing a sustained release dose of an effective amount of said clonidine over a subsequent period of 5 to 135 days, and the drug depot has a modulus of elasticity of about $2\times10^5$ to about $5\times10^5$ dynes/cm$^2$, and the drug depot is a gel having an inherent viscosity of about 0.10 dL/g to about 1.2 dL/g, and the drug depot further comprises an excipient comprising mPEG in an amount from about 0.001 wt. % to about 2 wt. % of the drug depot.

13. An implantable drug depot according to claim 12, wherein the drug depot is capable of releasing about 5% to about 100% of said clonidine relative to a total amount of clonidine loaded in the drug depot over the subsequent period of 5 to 200 days after the drug depot is administered.

14. An implantable drug depot according to claim 12, wherein said clonidine comprises about 10 wt. % to about 20 wt. % of the total wt. % of the drug depot and said polyorthoester comprises about 70 wt. % to about 99 wt. % of the total wt. % of the drug depot.

15. A method for treating acute pain, wherein said method comprises implanting a drug depot of claim 1 in an organism to reduce or treat pain, wherein said drug depot comprises clonidine in an amount from about 0.1 wt. % to about 30 wt. % of the drug depot, and a polyorthoester.

16. A method according to claim 15, wherein said clonidine comprises from about 5 wt. % to about 15 wt. % of the drug depot.

17. A method according to claim 15, wherein the drug depot is capable of releasing about 5% to about 100% of said clonidine relative to a total amount of said clonidine loaded in the drug depot over a period of 3 to 200 days after the drug depot is implanted in said organism.

18. A method according to claim 15, wherein said polyorthoester comprises at least 70 wt. % of the drug depot.

19. A method of making an implantable drug depot of claim 1, the method comprising combining a polyorthoester and a therapeutically effective amount of the clonidine and forming the implantable drug depot from the combination.

* * * * *

UNITED STATES PATENT AND TRADEMARK OFFICE
CERTIFICATE OF CORRECTION

PATENT NO. : 9,132,119 B2  
APPLICATION NO. : 12/412024  
DATED : September 15, 2015  
INVENTOR(S) : Hobot et al.

Page 1 of 1

It is certified that error appears in the above-identified patent and that said Letters Patent is hereby corrected as shown below:

In the specification,

In Column 22, Line 41, delete "theses" and insert -- these --, therefor.

In the claims,

In Column 25, Line 27, in Claim 1, delete "depot . . . is" and insert -- depot useful for reducing or treating pain in a patient in need of such treatment, the drug depot comprising a polyorthoester and a therapeutically effective amount of clonidine, the clonidine loaded in the drug depot in an amount of from about 1 wt. % to about 20 wt. % based on the total weight of the drug depot and the clonidine having a particle size range of from about 5 micrometers to about 250 micrometers and the drug depot being administered at a site beneath the skin of the patient to reduce or treat pain, wherein the drug depot is capable of releasing clonidine at an amount between 0.005 and 1.0 mg per day for a period of 5 to 135 days at the site and the drug depot has a region that releases an initial burst of clonidine in an amount of not more than 7 % of the clonidine loaded in the depot within five days, and the drug depot has a modulus of elasticity of about $2 \times 10^5$ to about $5 \times 10^5$ dynes/cm$^2$, and the drug depot is --, therefor.

In Column 25, Line 42, in Claim 5, delete "depot . . . is" and insert -- depot for reducing, or treating pain in a patient in need of such treatment, the implantable drug depot comprising clonidine loaded in the drug depot in an amount of from about 5 wt. % to about 20 wt. % based on the total weight of the drug depot and the clonidine having a particle size range of from about 5 micrometers to about 200 micrometers, and a polyorthoester, wherein the drug depot has a region that releases an initial burst of clonidine in an amount of not more than 7 % of the clonidine loaded in the depot within five days to a site beneath the skin, and the drug depot has a modulus of elasticity of about $2 \times 10^5$ to about $5 \times 10^5$ dynes/cm$^2$, and the drug depot is --, therefor.

Signed and Sealed this  
Twenty-sixth Day of April, 2016

Michelle K. Lee  
*Director of the United States Patent and Trademark Office*